United States Patent [19]
Greenberg

[11] Patent Number: 4,674,501
[45] Date of Patent: Jun. 23, 1987

[54] SURGICAL INSTRUMENT

[76] Inventor: I. Melbourne Greenberg, 62 The Hemlocks, Roslyn Heights, N.Y. 11576

[21] Appl. No.: 851,545

[22] Filed: Apr. 14, 1986

[51] Int. Cl.⁴ ............................................. A61F 17/32
[52] U.S. Cl. .................................... 128/305; 128/325
[58] Field of Search ............. 128/305, 312, 317, 318, 128/325, 321, 340, 355; 30/29; 403/92, 96, 327, 328

[56] References Cited

U.S. PATENT DOCUMENTS

| | | | | |
|---|---|---|---|---|
| 2,008,367 | 7/1935 | Rhinevault | ........................... | 403/328 |
| 2,741,248 | 4/1956 | Woodhall | ........................... | 128/317 |
| 3,585,985 | 6/1971 | Gould | ................................. | 128/318 |
| 4,084,594 | 4/1978 | Mosior | ................................ | 128/321 |
| 4,367,746 | 1/1983 | Derechinsky | ........................ | 128/325 |
| 4,440,170 | 4/1984 | Golden et al. | ....................... | 128/321 |

FOREIGN PATENT DOCUMENTS 3343867  6/1985  Fed. Rep. of Germany ...... 128/305

Primary Examiner—C. Fred Rosenbaum
Assistant Examiner—Ralph Lewis
Attorney, Agent, or Firm—Bauer & Amer

[57] ABSTRACT

A scissor-like assembly having a pair of axially mating and relative slidable elongated shafts each provided with a handle and include an articulating interconnection by which the shafts are simultaneously reciprocable relative to each other and conjointly movable about their common axis. Working tool members are provided at the end of each shaft.

4 Claims, 6 Drawing Figures

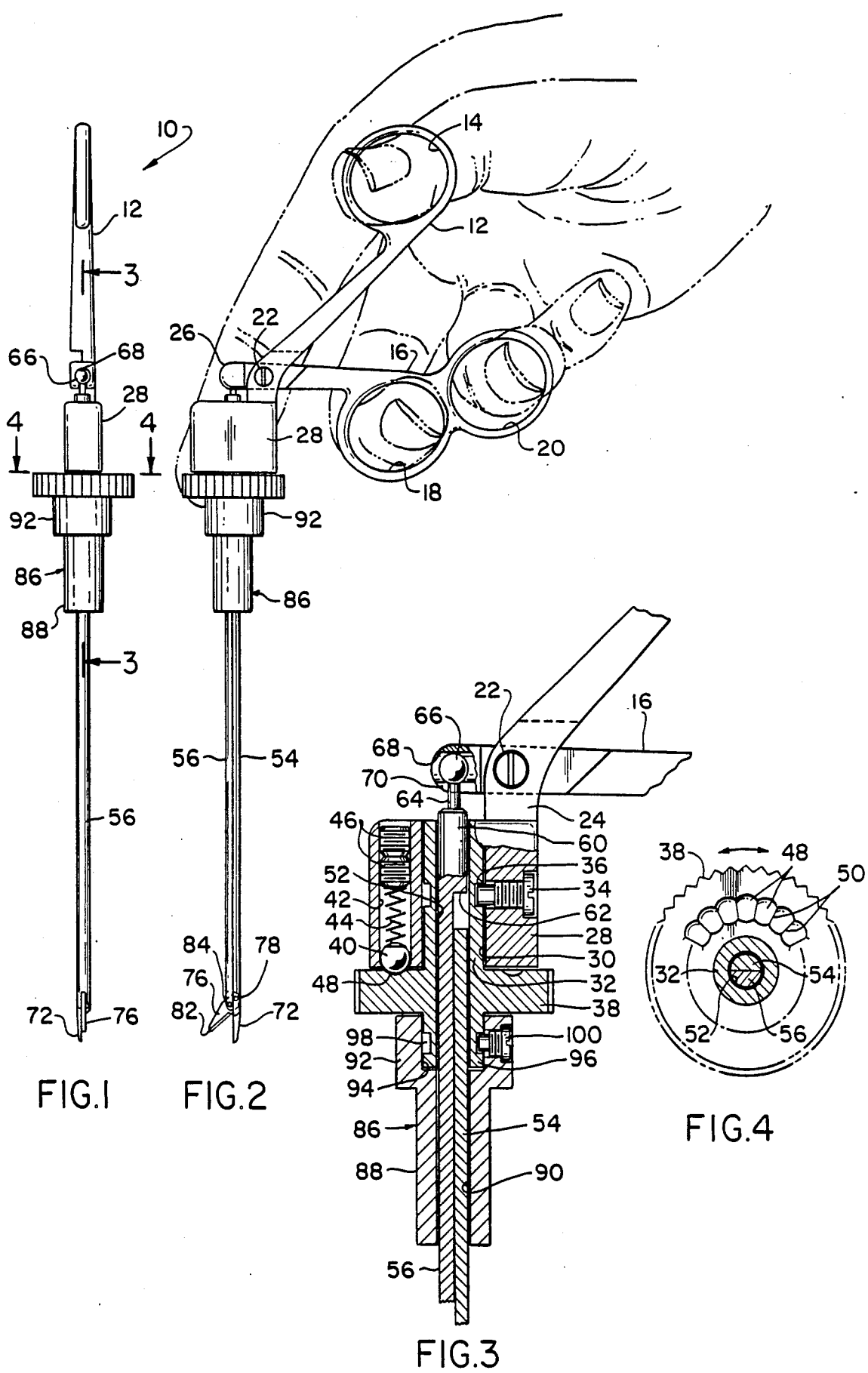

SURGICAL INSTRUMENT

BACKGROUND OF THE INVENTION

The present invention relates to a surgical instrument and in particular to an instrument for fine micro-surgery and endoscopic surgery.

A number of surgical instruments have been developed for use in micro-surgical and endosurgical procedures wherein it is impossible to make a large opening in the body although the instrument must be manipulated in various angles deep within the body. In general, such instruments comprise a fixed blade mounted at the distal end of a shaft and a moving blade mounted on the distal end of a linking rod that is slidable axially with respect to the shaft. The distal ends of the shafts are attached to a scissor grip handle for holding in a single hand. Manipulation of the handle causes the linking rod to in turn cause the movable blade attached to it to pivot in a shearing relationship with the fixed blade. Such devices are shown, for example, in U.S. Pat. Nos. 984,756; 1,754,806; and 3,585,985.

A disadvantage of the above examples lay in the fact that in order to adjust the direction of the working end relative to the axis of the combined shaft and rod from angle to angle, it was necessary for the surgeon to bodily rotate or move the entire instrument which necessitated twisting not only the instrument, but the hand and arm of the surgeon. Alternatively, the surgeon would remove his hand from the scissor grip and independently translate the position of the instrument from one direction to another and thereafter reinsert his hand on the scissor grip.

In U.S. Pat. No. 4,248,716 an instrument is disclosed which has as its purpose the avoidance of a structure wherein axially reciprocal rods and shafts are provided. In this patent, a rotatable rod is mounted within an elongated hollow shaft at the end of which are shearing members, which come into shearing engagement on the rotation of the internal rotatable shaft. In addition, the instrument has a barrel-like handle, a depressible finger mechanism and means for converting the linear motion of the finger mechanism into the rotary motion required to manipulate the rod. With this instrument, it was believed that the problem with regard to the orientation of the cutting end would be eased. However, this was, in fact, not obtained since the blades still were fixed in position relative to the axis of the instrument and the surgeon still had the disadvantage of having to bodily rotate the instrument into a particular angular position as well as the added disadvantage of having to depress a finger mechanism against a barrel-type handle.

A similar device is disclosed in U.S. Pat. No. 4,433,687 in which a micro-surgical instrument is shown wherein two sections of a barrel handle are compressed to rotate an inner mechanism whose rotary motion is converted into a linear motion to draw a pair of blades together. This device has not had any commercial success, suffering from the same disadvantage as the other exemplary disclosures.

It is an object of the present invention to overcome the disadvantages of the prior art micro-surgical devices and to provide an instrument which is efficient, easy to use in a single hand, and wherein the angle of attack of the working tools are readily adjusted by single finger manipulation, independently of the motion causing shearing action.

A further object is to provide a surgical instrument having a simple reciprocating rod and shaft mechanism of extremely small diameter that can be inserted into a relatively small field of operation without undue trauma or disruption of tissue, and which is easily oriented in situ.

It is a further object of the present invention to provide a surgical instrument which is operable in a single scissor hand grip in a manner familiar to and with which the surgeon has a great deal of experience.

These objects and advantages together with others will be apparent from the following disclosure.

SUMMARY OF THE INVENTION

According to the present invention a surgial instrument is provided comprising a fixed shaft and an axially mating and slidable shaft associated therewith. Each one of said shafts has a tool member at one end and a handle mechanism including a part of a scissor grip at the other end. The handle mechanism includes means for articulatingly connecting the shafts to effect relatively slidable movement therebetween and permit conjoint rotation of the shafts about their common axis.

Preferably the interconnecting means is such that conjoint rotation of the shaft and rod is effected relative to the scissor grip and is effected by manipulating the shaft and rod by an extending finger of the surgeon, and has cooperating detent means defining the conjoint rotation of the shafts at predetermined intervals.

Specifically, each of the shafts has a semi-circular cross section and they are arranged so that their flat diametric surfaces are in mating slidable abutment. A short sleeve is mounted over the proximal end of the shafts, and is fixedly attached to one shaft, while permitting the other shaft to extend freely through it to be exposed at its extreme proximal end, outward of the sleeve. A pair of scissor-type handle members pivotally attached to each other are provided; one handle being attached directly to the sleeve for conjoint axially movement, and simultaneous relatively free rotary movement therewith; while the other handle is universally attached to the proximal end of the movable shaft so that it may turn freely in any direction with regard to the handle. Opening and closing of the handle members, therefore, produces reciprocal motion between the shafts within the sleeve while simultaneously permitting the sleeve, the shaft fixed to the sleeve, and the movable shaft mating therewith to rotate about the central axis of the shafts.

The sleeve and handles are arranged so that the sleeve is manipulatable by an extending finer not used in the scissor grip and is preferably provided with a peripheral indexing wheel for convenience of manipulation. Arranged in combination with the indexing wheel are cooperating recess and detent means, by which the intervals of indexing are determined and fixed so that once positioned in the proper position, the surgeon is assured that the instrument will maintain its position.

Full details of the present invention are set forth in the following description of the preferred embodiment and illustrated in the accompanying drawings.

BRIEF DESCRIPTION OF THE DRAWINGS

In the drawings:

FIG. 1 is a front elevational view of a surgical scissors employing the present invention;

FIG. 2 is a side elevational view of the instrument as shown in FIG. 1;

FIG. 3 is a sectional view of the instrument taken along lines 3—3 of FIG. 1;

FIG. 4 is a sectional view of the instrument taken along lines 4—4 of FIG. 1;

DESCRIPTION OF THE INVENTION

Figures 5, 6:
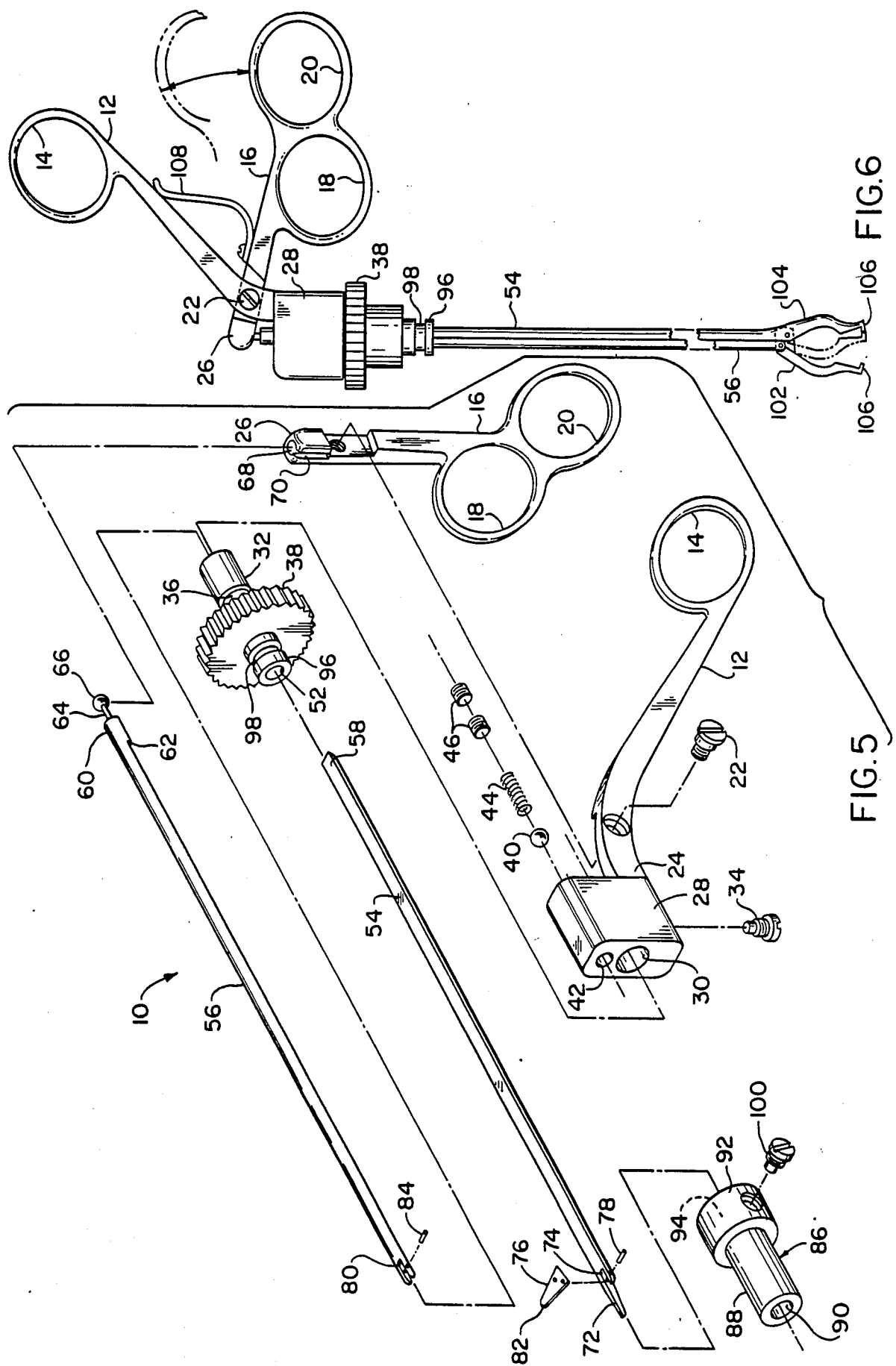
FIG. 5 is an exploded isometric view of the instrument of FIGS. 1–4 showing various elements in detail.
FIG. 6 is a side-elevational view showing an aneurysm clip holder embodying the present invention.

As illustrated in FIGS. 1–5, the surgical scissor embodying the present invention is generally depicted by the numeral 10 and includes a main scissor grip handle member 12 having a thumb hole 14 and an auxiliary scissor grip handle member 16 having second and third finger holes 18 and 20. The two handle members 12 and 16 are pivotally joined about a horizontal axis by a pivot screw 22, so as to be movable angularly with respect to each other in a plane perpendicular to the pivot axis. The main handle member 12 and the auxiliary handle member 16 are provided with extending arms 24 and 26 respectively which extend perpendicularly to each other and which have recessed surfaces so that one fits with the other about the pivot pin 22 to form the scissor plane.

Integrally formed at the end of the extending arm 24 of the main handle 12 is a rectangular block 28 having its large surfaces generally parallel to the plane in which handle members move. Extending through the center of the block 28, in a direction parallel to that of the arm 24 of the main handle 12 is an enlarged bore 30 in which is located and elongated rotatable sleeve 32. The sleeve 32 is held in the block 28 by a screw 34 which passes through the narrow end wall of the block 28 into an annular groove 36 formed on the outer surface of this sleeve 32. In this manner, the sleeve 32 is rotatable relative to the block 28 and consequently to the handle member 12 while being conjointly movable in the axial direction therewith. Located at the lower end of the sleeve 32 is a radially enlarged indexing wheel 38 by which the sleeve 32 may be rotated, as seen in FIG. 2, by the normally free indexing finger of the user. A detent mechanism for insuring the stepwise rotation of the sleeve 32 is provided and comprises a ball 40 located in a through bore 42 extending through the block 28, parallel to the central bore 30, on the side opposite that of the set screw 34. A biasing compression spring 44 acts on the ball 40, and a set screw 46 abuts the compression spring 44 and maintains the spring 44 and ball 40 within the bore 42. The upper surface of the indexing wheel 38 is, as seen more clearly in FIG. 4, provided with a plurality of circular recesses 48 arranged in a single annulus about the center of the indexing wheel 38 in alignment with the spring loaded ball 40 which is adapted to seat within a given recess 48 while the sleeve 12 is movable, on rotation of the indexing wheel 38 from recess to recess.

The circular recesses 48 formed on the surfaces of the indexing wheel 38 are arranged at eighteen (18) degrees from center to center so that twenty (20) recesses can be normally provided on a disk, thus providing twenty individual indexing intervals. Should it be found necessary to employ a lesser or greater number of indexing intervals, the arrangement of recesses can be varied as will be obvious to those skilled in the art. In addition, the intermediate ridges 50 between adjacent recesses 48 can themselves be flattened and formed with a slight flat or curved plane to retain the spring-loaded ball 42 in a position between the adjacent recesses 48.

Extending outwardly from the central bore 52 of the sleeve 32 is a pair of shafts 54 and 56, both of which are semicircular in cross section and have a combined outer diameter only slightly smaller than that of the central bore 52. The shafts 54 and 56 are arranged in abutment with each other so that their flat diametric surfaces are movable axially one over the other. The first shaft 54 is slightly shorter than the second shaft 56 and is fixedly attached at its proximal end 58 to the inner surface of the sleeve 32 by conventional welding, brazing, or other means. The second shaft 56 is provided with an enlarged cylindrical head 60 conforming to the diameter of the inner bore 52 of the sleeve 32 so as to form a shoulder 62 extending over the proximal end 58 of the fixed shaft 54 so that the relative inward movement of the second shaft 56 with respect to the fixed shaft 54 can thus be limited.

Extending outwardly from the cylindrical head 60 of the movable shaft 56 is a short pedestal 64 at the end of which is integrally formed a ball 66 which fits within a cylindrical hole 68 in the arm 26 of the auxiliary handle 16. The hole 68 opens inward in the axial direction from the extreme end of the arm 26 and is provided a slot 70 which together form a keyhole passage allowing the pedestal 64 and ball 66 to slide freely, relative to the handle 16. In this way, the ball 66 and the keyhole passage, formed by the hole 68 and slot 70, form a universal joint permitting the auxiliary handle member 16 to be manipulated so as to carry the movable shaft 56 in a reciprocal direction within the sleeve 32 without binding or bending in the handle 16 or in the sleeve 32.

As seen more particularly in FIG. 5, the shaft 54 fixed to the sleeve 32 is integrally formed with a fixed blade member 72 and with an adjacent narrow slot 74 in which is received a movable blade 76, held by a pivot pin 78. The movable shaft 56 is provided at its distal end with a bifurcated slot 80 which passes about the edge of the movable blade 76 at a point intermediate the pivot pin 78 and its outer tip 82 and is pivotally held in this position by a second pivot pin 84.

In operation, the surgeon holds the instrument as a conventional scissor, manipulating the handles to effect cutting. As previously pointed out, the movable shaft 56 is reciprocable relative to the fixed shaft 54. When such reciprocation is effected by operation of the scissor-grip handles, the movable shaft 56 produces a shearing action between the blades 72 and 76. When the angle of attack or the position of the blades must be changed, the fixed shaft 54 and the movable shaft 56 are conjointly rotatable about their common central axis by rotating the sleeve 32 relative to the block 28. Since the stationary shaft 54 is fixed to the sleeve 32, its flat surface abutting the flat surface of the movable shaft 56 causes the movable shaft to rotate conjointly with it, whether or not the movable shaft 56 is being reciprocated. That is, the rotation of the shafts 54 and 56 can be made simultaneously with or independently of the relative axial movement between the shafts. Such independent and/or conjoint movements are assured, without any hindrance, through the use of the universal joint created by the ball 66 and the keyhole formed by the hole 68 and the slot 70.

Consequently, the surgeon may manipulate the surgical instrument free of worry or care simply by the use of a single hand, three fingers of which securely effect the shearing action at the distal end while the normally free indexing finger effects the rotation of the shaft and thus the angular disposition of the cutting blades within the body.

If the desired by the surgeon, the instrument can be provided with an adaptor 86 by which he can hold or guide the instrument with his non-working hand so as to provide a completely steady action on the instrument without interfering with the operation of the shafts. As seen in FIG. 3, the adaptor 86 comprises a second sleeve 88 having an inner bore 90 fitting about the shafts, and an enlarged head 92 having a larger inner bore 94 fitting over the extending portion 96 of the indexing sleeve 32 below the indexing wheel 38. The lower end 96 of the sleeve 32 is provided with an annular groove 98 into which a set screw 100 passes, allowing the adaptor 86 to move in the axial direction conjointly with the indexing sleeve 32 while being freely rotatable relative to the indexing sleeve.

FIG. 6 illustrates the principles of the present invention as adapted in the contruction of an aneurysm clip holder. In this figure the same parts bear the same numbers as in FIGS. 1 to 5; the blades 72 and 76 being, however, replaced with a pair of clip holders 102 and 104. The first clip holder 102 is integrally formed at the end of the fixed shaft 54 while the second holder 104 is pivotally attached to both the movable shaft 56 and the fixed shaft 54, in the same manner as earlier described with regard to blades 72 and 76. Both holders 102 and 104 are arcuately shaped, and have ends 106 which are adapted to come into face to face clamping action, whereby a clip (not shown) may be held and secured in place.

FIG. 6 also illustrates another modification in that a leaf spring 108 may be provided having one end attached to the auxiliary handle member 16 and its other end abutting against the main handle member 12. In this manner the handle members 12 and 16 are biased apart, resulting in the consequent normally biased opening of the holders 102 and 104. While not shown in the scissor embodiment of FIGS. 1 to 5, it will be obvious that the spring 108 can be used there with equal effectiveness.

In addition to scissors and forceps, other tool members may be employed to provide punches, forceps, needle holders or Rongeurs or other instruments, without otherwise departing from the concept of the present invention.

Various modifications, changes and embodiments are shown and described herein; others will be obvious to those skilled in this art. Accordingly, it is intended that the foregoing be illustrative only and not limiting of the scope of the invention.

What is claimed is:

1. A surgical instrument comprising a pair of axially matable and relatively slidable shafts each having at their distal ends cooperating working tools, a sleeve mounted adjacent the proximal end of said shafts, one of said shafts being fixedly attached to said sleeve for conjoint movement therewith, the other of said shafts extending freely through said sleeve and being exposed at its proximal end, a pair of handle members pivotally attached to each other and arranged scissor-like for manipulation by one hand, one of said handles being attached to said sleeve for conjoint axial movement and relative free rotary movement therewith, said sleeve and said one handle being arranged so that said sleeve is manipulatable by a finger of the same hand simultaneous with the manipulation of said handle, a radially enlarged wheel on said sleeve and said wheel and said one handle having a cooperating detent mechanism defining the conjoint rotation of said shafts in predetermined intervals, said other handle being universally attached to the exposed proximal end of said freely extending shaft, said shafts being caused to reciprocate relative to each other on manipulation of said handle members and to rotate about their common axis by manipulation of said sleeve, whereby said tools may be operated and moved into selected rotary positions relative to the axis of said shafts.

2. The surgical instrument according to claim 1, wherein said tools comprise shearing elements.

3. The surgical instrument according to claim 1, wherein said tools comprise clip holding and clamping elements.

4. The surgical instrument according to claim 1 including a second sleeve located about said shafts below said first mentioned sleeve and attached thereto to permit relative rotary movement and conjoint axial movement therewith.

* * * * *